United States Patent [19]

Mantz

[11] 4,086,652
[45] Apr. 25, 1978

[54] METHOD AND APPARATUS FOR ANALYZING A TIME-DEPENDENT PHENOMENON

[75] Inventor: Arlan Warren Mantz, Acton, Mass.

[73] Assignee: Block Engineering, Inc., Cambridge, Mass.

[21] Appl. No.: 760,701

[22] Filed: Jan. 19, 1977

[51] Int. Cl.² .......................... G01V 1/28; G01B 9/02
[52] U.S. Cl. ............................... 364/525; 356/106 S; 364/819
[58] Field of Search ............... 235/151.3, 151.35, 183; 356/106 S

[56] References Cited

U.S. PATENT DOCUMENTS

| 3,556,661 | 1/1971 | Hepner | 356/106 S |
| 3,924,952 | 12/1975 | Marechal et al. | 356/106 S |
| 3,989,938 | 11/1976 | Auth | 356/106 S |

Primary Examiner—Malcolm A. Morrison
Assistant Examiner—Errol A. Krass
Attorney, Agent, or Firm—Schiller & Pandiscio

[57] ABSTRACT

A system for analyzing a time-varying phenomenon in which the latter is repetitively initiated and a spectral output is generated during the course of each successive phenomenon. The output spectrum is repetitively scanned by a fast Fourier transform interferometer to produce an interferogram. The time relation between a selected retardation point in the interferometer and the initiation of each phenomenon is successively shifted so as to produce an ordered set of interferograms each representing a different time relation between initiation and scanning. Data corresponding to a selected temporal resolution element having a fixed time position following initiation of the phenomenon are selected from each of the ordered set of interferograms and the selected data are then reassembled in the same order as the interferograms from which they were taken, to produce a synthetic interferogram. The synthetic interferogram, when inversely transformed, provides the spectrum of the phenomenon as it appeared during that selected temporal resolution element.

13 Claims, 4 Drawing Figures

METHOD AND APPARATUS FOR ANALYZING A TIME-DEPENDENT PHENOMENON

This invention relates to systems for time-resolving data, and particularly to the time resolution of data multiplex-encoded into a single channel.

For example, conventional analysis of spectral phenomena typically involves a plurality of observations of each spectral element over a period of time. Such observation can be made in parallel along a like plurality of channels or can be made sequentially over a single channel. Effectuation of such a series of sequential observations is highly inefficient because the total time during which any one resolution element (e.g. a particular wavelength band) can be observed practically is quite limited. Additionally, the observation of each resolution element implies that all of the other data are discarded or unused during the particular observation time. A resolution element here can be defined as the number of samples to be taken of a phenomenon, divided by the total time required to obtain the totality of samples.

Fourier transform spectroscopy provides a substantial improvement over the classical dispersive techniques exemplified by a conventional spectrometric single channel method. A Fourier transform spectrometer provides a sequence of data generated on a single channel and arising from the modulation of all wavelengths of input light with a separate carrier frequency. The separate wavelengths can then be discriminated from one another by frequency filtering, the amplitude of each frequency being proportioned to the intensity of the light as the wavelength corresponding to that frequency. Such an interferometer spectrometer can thus measure each wavelength for a time N/2 (where N is the number of resolution elements) longer than the time required to obtain similarly resolved measurements with conventional spectroscopes. The improvement in accuracy gained by using an interferometer spectrometer (i.e. the square root of N/2) is known as Felgett's advantage or the multiplex advantage, and is described in detail by L. Mertz, *Transformations in Optics*, Chap. I, John Wiley & Sons, Inc., (1965). Such Fourier transform spectroscopes usually either employ stepping interferometers with gated detector signals or incorporate rapid scan techniques. The former imposes severe limits on instrument stability as well as source life time; the latter imposes severe limits on maximum achievable resolution, signal-to-noise ratio and time resolution. Spectroscopy with a rapid scan interferometer has been considered most useful with steady-state or quasi steady-state light sources because, as Mertz points out, where there is source modulation, the noise level increases by N/2, as compared with Felgett's advantage of square root of N/2, leaving a net inferiority of a factor of the square root of N/2. In effect, the modulation of the source is considered to act as a factor similar to a truncating function. For the foregoing reasons, the use of Fourier transform spectroscopy to examine time-varying spectral phenomena has been largely neglected despite the extremely efficient throughput of a Fourier transform spectroscope.

R. E. Murphy et al in "Time-Resolved Fourier Spectroscopy" Journal of the Optical Soc. of America, Vol. 65, No. 5, May, 1975, pp. 600–605 suggests that Fourier spectroscopy can be used to investigate time-dependent spectral sources. Murphy et al observed with an interferometer-spectrometer a series of phenomena each at a different fixed path retardation, synthesized from the data a set of time sequenced interferograms and transformed the time-sequenced interferograms to obtain the recovered spectra at successive time intervals. However, the Murphy et al technique, using stepped retardation, is subject to the limitations on instrument stability and source life time above noted and is highly sensitive to amplitude variation among the several phenomena observed.

The present invention overcomes problems of the prior art by employing both temporal and spectral multiplexing with a transform system which allows high resolution and signal-to-noise even with data with microseconds resolution time. A principal object of the present invention is therefore to provide means for and a method of analyzing transient phenomena using both temporal and spectral multiplexing. While the system can be used with any of a large number of data gathering devices (such as pulsed NMR and NQR systems, Hademard spectrometers and the like) particularly, the present invention has as an important object the use of a continuous scanning Michelson interferometer for spectral study of kinetic systems using both temporal and spectral multiplex techniques.

To effect the foregoing and other objects, the present invention generally is embodied in a system for time resolving a sequence of data derived from a phenomenon, which system comprises repetitive initiation of the phenomenon, detection of each occurrence or cycle of the phenomenon and the repetitive convolution with a transformation (as by continuous, controlled-velocity, repetitive, interferometric scanning) to provide an ordered set of interferograms each being representative of the course of each cycle of the phenomenon. By establishing the repetitive scanning cycle and the repetition of phenomenon initiation at different repetition rates, the scanning, and excitation cycles therefore are shifted in time in ordered increments with respect to one another preferably until the initial temporal relation between initiation and sampling is restored. The term "interferogram" as herein used refers particularly to a self-reciprocal transform of a time sequence of input data, e.g. a Fresnel, Fourier, Dirac or other such transformation where the input data are spectral, sonic or the like. From the first set of interferograms, at least one "time average" interferogram is synthesized from a plurality of data moieties or points, each being at the same selected fixed position (in time) on each of the first set of interferograms with regard to initiation of the phenomenom. The "time averaged" interferogram (or second set of interferograms as the case may be) is then analyzed or subjected to the inverse of the initial transform to produce a data set representing the phenomenon as it occurred at that fixed data point in time following initiation of the phenomenon, i.e. the data set is constant in "source" time.

Other objects of the invention will in part be obvious and will in part appear hereinafter. The invention accordingly comprises the apparatus and method possessing the construction, combination of elements, and arrangement of parts which are exemplified in the following detailed disclosure, and the scope of the application of which will be indicated in the claims. For a fuller understanding of the nature and objects of the present invention, reference should be had to the following detailed description taken in connection with the accompanying drawings wherein:

The present invention can advantageously be described typically in connection with scanning interferometric means as an exemplary means for generating interferograms each being representative of at least some stage in the progression of a phenomenon being observed. The latter, for exemplary purposes here, will be considered to be the photolytic decomposition of acetone vapor by ultraviolet radiation, although it should be appreciated that a very large number of phenomena are susceptible of analysis of the present system. For example, the invention can be employed in basic chemical kinetics studies, isotopic separation processes, laser fusion phenomena, photochemical ionization and free radical phenomena, relaxation phenomena and the like. The present invention is particularly useful in study and analysis of processes in which excitation occurs within $10^{-6}$ to $10^{-8}$ seconds, and after approximately $10^{-4}$ seconds the excited medium relaxes within about a $10^{-3}$ to $10^{-1}$ second period.

Figure 1:
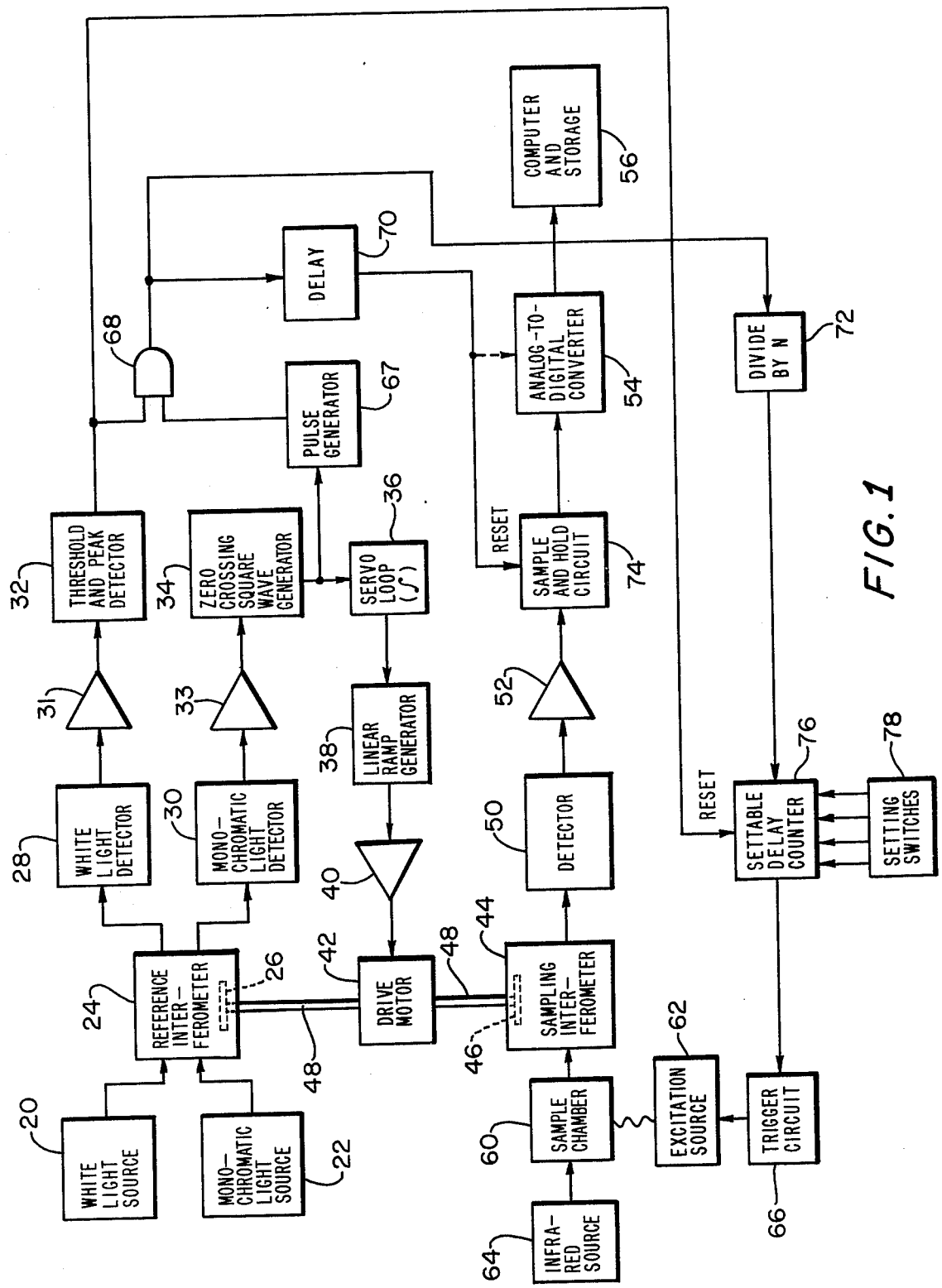
FIG. 1 is a schematic block diagram of a system embodying the principles of the present invention.

As a typical scanning interferometeric means, one can use a Digilab Model FTS-20, commercially available from Block Engineering, Inc., Cambridge, Mass. As shown in FIG. 1, such an interferometeric means typically includes white light source 20 and monochromatic light source 22, both positioned to illuminate the entrance aperture of reference interferometer 24. The latter typically is a Michelson interferometer in which the scanning element serving to modulate input radiation to provide an interferogram thereof, is a movable mirror shown schematically at 26.

Positioned in known manner to detect the modulated interference pattern produced by reference interferometer 24 are broad band white light detector 28 and monochromatic light detector 30, it being understood that these detectors include any filters necessary to discriminate between the interference patterns respectively produced in response to the respective light sources. White light detector 28 typically produces an electrical signal as a function of the white light interference pattern or interferogram generated by reference interferometer 24. The electrical output of detector 28 is coupled to the input of amplifier 31 and the output of the latter is connected to the input of a threshold-and-peak detector circuit 32.

Similarly, detector 30 provides an electrical signal as a function of the light input thereto, so the electrical output of detector 30 is coupled to the input of amplifier 33. The output of amplifier 33 is connected as an input to zero-crossing square wave generator 34. The latter typically is simply an axis-crossing detector circuit, the output of which is coupled to the input of a monostable multivibrator or one-shot to trigger the latter to produce a square wave when an axis-crossing is detected. Both circuits being well known in the art so need no further delineation. The output of axis-crossing detector 34 is connected to the input of integrating servo loop circuit 36. The output of servo loop circuit 36 is connected to the input of linear ramp signal generator 38. The output of the latter is connected through power amplifier 40 as the input to drive motor 42, typically a solenoid-type reciprocating motor.

The interferometric means also includes sampling interferometer 44, substantially the same as reference interferometer 24, in which the scanning element which serves to modulate input radiation is shown schematically and typically as mirror 46. Both mirror 46 and mirror 26 are connected by a mechanical coupling (shown schematically at 48) to motor 42 so as to be driven synchronously by the latter.

Disposed with respect to interferometer 44 so as to detect the interference pattern or interferogram produced by the latter, is detector 50 which serves to convert the optical interferogram into a corresponding electrical signal. The electrical output of detector 50 is coupled through amplifier 52 to the input of analog-to-digital converter 54, and the output of the latter is connected through appropriate interfacing (not shown) to computer 56. The interferometeric means thus described is essentially the prior art basic structure of the aforesaid commercial FTS-20 device. Computer 56 is typically a Nova Model 2/10 computer (commercially available from Data General Corporation, Southboro, Massachusetts coupled to a 1.2 million word moving head disc for temporary data storage and a digital magnetic tape for permanent data storage and constitutes a convenient form of means for selecting from each interferogram of an ordered set, a data point corresponding to a time resolution element or interval occurring at a fixed time position following initiation of the phenomenon, and for combining the data points in the same order as the ordered set to synthesize a second interferogram representing the convolved data only at that time position. It will be apparent to those skilled in the art that a dedicated special purpose digital computer or hard-wired analog system could readily be substituted in place of computer 56.

The means for repetitively initiating the phemonemon to be analyzed includes sample chamber 60 in which the phemonemon is to be initiated, and triggerable excitation source means 62 for exciting the phemonenon of interest in chamber 60 at selected times. Typically, chamber 60 is an enclosure such as a 30 centimeter long quartz absorption cell equipped with KBr windows to permit detection of the phenomenon by infrared absorption. To this end, infrared source 64 is disposed for illuminating sample chamber 60 such that interferometer 44 can modulate infrared radiation emitted from chamber 60 following any infrared absorption occurring in the course of the phenomenon. Excitation source means 62 can be any of a number of systems, but typically, for the example of photolytic decomposition chosen here, is a triggerable ultraviolet flash lamp system such as a 1540 Strobolume system (commercially available from General Radio Company, Concord, Mass.) which can provide a ¼ joule output intensity $10\mu$ sec. full width, half-maximum light pulse.

Source 62 is also connected to be controlled by trigger circuit 66. Thus the source can be triggered at any selected time at any of a number of selected rates. The output of generator 34 is connected to the input of pulse generator 67, typically a Schmitt trigger circuit, the output of the latter being connected together with the output of detector circuit 32 as inputs to AND gate 68. The output of the latter is connected to the inputs of both delay circuit 70 and divider 72. Delay circuit 70 which simply serves to introduce, in known manner, a time delay into signal propagation, has its output connected to the reset input terminal of sample-and-hold circuit 74.

The system of the present invention provides means for converting into digital form each sequence of data produced by interferometer 44. To this end, the data input terminal of circuit 74 is connected to the input of analog-to-digital converter 54, so that circuit 74 serves as a sampling linkage between interferometer 44 and computer 56.

Divider 72, a typical digital "divide-by-N" circuit, has its output connected to the count input of a settable delay means such as counter 76. The count in the latter is typically controlled or selected by manually operable setting switches 78 such as thumb wheel switches or the like. Lastly, the output of detector circuit 32 is also connected as an input to the reset terminal of counter 76.

Figure 2:
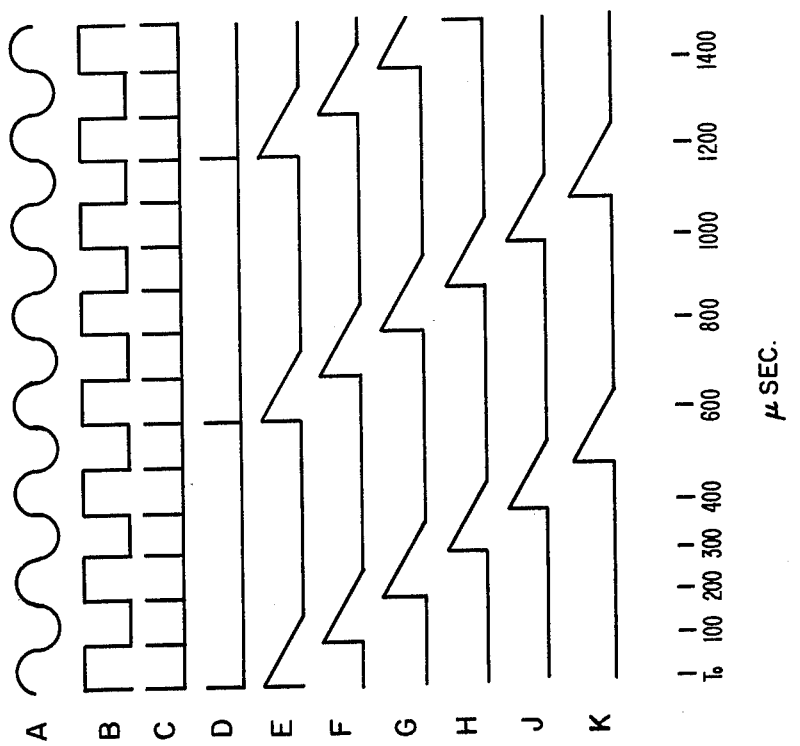
FIG. 2 is a number of representative idealized waveforms on a common time base, of signals appearing at various points in a system of the type shown in FIG. 1.

In operation, drive motor 42 is driven by a linear ramp or sawtooth signal from generator 38 so that mirrors 26 and 46 have a displacement velocity of approximately 0.3cm/sec. The light from source 22 (typically an HeNe laser which provides an output at 6328 A) is modulated by the motion of mirror 26, and because the mirror motion is linear, detector 30 and amplifier 33 provide a sinusoidal output (shown schematically at FIG. 2A) with a period of approximately 100 microseconds. Similarly, white light detector 28 will provide a well known white light interferogram as the path retardation of interferometer 24 changes with the motion of mirror 26. Such a white light interferogram characteristically possesses a maximum or peak intensity at the point of zero path retardation. The output of amplifier 33 is converted in generator 34 to a square wave such as shown in FIG. 2B. The square wave output of generator 34 is applied to the input of circuit 36 wherein the square wave is integrated. Thus, the output of circuit 36 will provide a zero signal when the duty cycle of the input square wave is exactly 50 percent, but any variation in the duty cycle will result in a corresponding error signal being provided at the output of error signal 36. This error signal when applied to linear ramp generator 38, changes the slope of the ramp provided by generator 38 in such a direction as to alter the velocity of mirrors 26 and 44 so as to restore the duty cycle of the output of generator 34 to precisely 50 percent. The system, therefore, constitutes a closed loop which insures that the frequency of the output of generator 34 is closely maintained at the desired value.

Detector circuit 32 provides an output signal which serves to enable gate 68 only at some time, $t_0$, the zero path retardation peak seen by detector 28. Hence, all timing in the system can be controlled to operate from the point of zero retardation in each scanning cycle provided by interferometer 24. It will be appreciated that at the end of each excursion of mirror 26, a scanning cycle of the interferometer has been completed and that the interferometer must be reset. The controls which reset ramp generator 38 and reverse drive motor 42 and reset the output of detector 32 are not shown for the sake of clarity in exposition, but are well known and are part of the typical interferometer-spectrometer currently commercially available.

When gate 68 is enabled at $t_0$, it passes a train of clock pulses produced by pulse generator, each pulse representing an axis crossing of the square wave produced by generator 34. A typical train of pulses is shown in timed relation in FIG. 2C. The pulse train is applied to divide-by-$n$ circuit 72 which, therefore, provides an output pulse train, such as is shown in FIG. 2D wherein $n = 6$ for exemplary purposes, having a repetition rate which is $1/n$ of the repetition rate of the output of gate 68. The pulse train of FIG. 2D is applied, after having been passed through delay 76, to actuate trigger circuit 66 and excite source 62 into emission. The output of excitation source 62 is shown schematically in FIG. 2E wherein the signal or flash, corresponding to the triggering pulse of FIG. 2D, rises to a maximum and and then decays to a minimum, for example, with full width at half-height of 100 microseconds. The period between pulse or initiation of the output of excitation source is, of course, 600 microseconds, corresponding to the pulse repetition rate of the output of circuit 72. This sequence of events continues with the excitation source being triggered at 600 microsecond intervals until the end of an interferometer scan in interferometer 44, whereupon the pulse train from gate 68 is terminated until the next scan has commenced and an appropriate synchronizing axis-crossing just after a zero retardation peak detection by detector 32 has occurred. Each excitation flash occurring during an interferometer scan initiates the phenomenon of interest, e.g. the photolytic decomposition of acetone in chamber 60. During the course of the decomposition, the spectral changes due to absorption of infra-red from source 64 are observed by interferometer 44 which convolves the observed spectrum with a fast Fourier transformation to produce, as well known, an interferogram. In order to provide an acceptable signal-to-noise ratio, a number of identically scanned interferograms can be coadded either through analog methods as described in U.S. Pat. No. 3,286,582 to L. Mertz, or by conversion to digital form and addition in the computer. In the example here described, the interferogram collected in one complete scan with a duration from zero retardation of 0.12 seconds, would include data derived from about 200 excitation source flashes. The number of excitation source flashes per interferometer scan, (or the number of scans per flash as the case may be) depends upon the relative length of time during which the phenomenon of interest continues (or decays) and the time period of the scan cycle, so the ratio of flashes to scans is largely a matter of choice.

Delay counter 36 is then set by setting switches 78 to interpose a one pulse period (100 microsecond) delay so that the time history of the subsequent excitation source pulses becomes as shown in FIG. 2F, i.e. is shifted by a time increment with regard to the zero retardation peak position of the interferometers. When sufficient interferograms have been obtained using the sequence of flashes of FIG. 2F, and appropriately coadded to improve signal-to-noise, the delay in counter 76 is again reset by adding another 100 microsecond delay period resulting in a time history of excitation source outputs somewhat as shown in FIG. 2G. Similarly, by altering the delay provided by counter 76 by successive 100 microsecond increments, one obtains an ordered set of excitation pulse histories such as is shown in FIGS. 2H, J and K. It will be appreciated then that for each of the excitation source histories shown in FIGS. 2E through 2K inclusive, one obtains a similarly ordered set of corresponding interferograms. These interferograms contain all of the source spectral information and the source temporal history with a 2 microsecond resolution, each resolution element being displaced by 100

μsecs from the next resolution element of 2 μsec. Interferograms as produced at the output of detector 50 and amplified by amplifier 52 are, in well-known manner, sampled by sample-and-hold circuit (preferably using a 2 microsecond or less interval) and each sample is converted by analog-to-digital converter 54 to digital form for storage as an ordered set in computer 56.

Preferably, delay 70 is adjustable by 0.5 μsec increments to fine tune by interposing a delay in actuating sample-and-hold circuit by the 100 μsec period pulse train from gate 68. This serves to permit sampling of data to be delayed, relative to triggering of excitation source 62, to match or compensate for the usual rise time of the phenomenon in response to excitation.

From the data thus provided and stored in computer 56, one however can look at the spectrum of material in sample chamber 60 within a 2 microsecond resolution range or time domain. For example, if one wishes to look at the nature of the spectrum in the 0–100 microsecond time domain, one takes the data moieties or information taken during the first, seventh, thirteenth, etc., resolution elements (each of 2 microsecond duration) from the first interferogram corresponding to the excitation due to the excitation source history shown in FIG. 2E; the data moieties from the second, eighth, fourteenth, etc., resolution elements of the interferogram next in order and corresponding to the source history shown in FIG. 2F; the information taken during third, ninth, fifteenth, etc. resolution elements of the interferograms third in order and corresponding to the excitation source history of FIG. 2G, etc. until all stored interferograms have been sampled, and construct a new or synthetic interferogram in which each of the data moieties are placed in sequence according to the order of the original interferograms in the set. The software sorting routine needed to construct a synthetic interferogram corresponding to one time-resolution element can be constructed in the following manner, using a notation in which a letter in parentheses identifies the original interferogram by the letter caption of the excitation source history of FIG. 2, and the number in the parentheses is the ordinal value of $t_o$ from the selected time resolution element in units of 100 microseconds. For example, the notation for the temporal resolution element at 400 μsecs after $t_0$ in the interferogram, corresponding to the temporal source history shown in FIG. 2G would be (G,4). Thus, synthetic interferogram for the first 100 microsecond interval of the original interferograms would be constructed by placing in sequence the data corresponding to the following (E1) (F2) (G,3), (H,4), (J,5), (K,6), (E,7), (F,8), (G,9), (H,10), (J,11), (K,12), etc. A formal software program for effecting the foregoing in a Data General 2/10 computer is attached hereto as appendix A.

Once an interferogram has been synthesized and stored again in the computer, the latter is preferably programmed to perform the inverse transformation on the synthetic interferogram to obtain the information, such as the spectrum, as it was observed during the time interval or resolution element to which the synthetic interferogram corresponds. The programs required to perform a fast Fourier transformation by digital computer, such as the Cooley-Tukey algorithm well known in the art. Alternatively, in place of a digital computer, one can use an analog system such as heterodyne wave analyzer to perform the desired inverse transformation.

Figure 3:
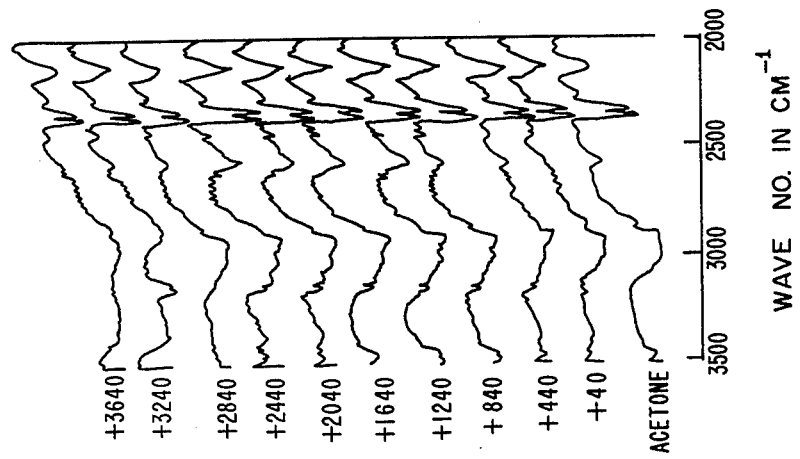
FIG. 3 shows representative spectra obtained by transformation of interferograms synthesized from other interferograms taken during photolytic decomposition of acetone.

The above detailed invention was used to investigate ultraviolet photolysis of a number of materials, particularly acetone and acetaldehyde. Using the flash lamp hereinbefore described as source 62, one obtained quarter joule peak intensity, 10 μsec full width half-maximum light flashes. The flash lamp operated at 250 flashes per second. A series of interferograms were taken and synthetic interferograms were formed and inversely transformed. The various time-dependent spectra are shown in FIG. 3, each representing a 2 μsec interval, 400 μsecs apart, each identified by the time in microseconds from $t_o$. The bottom spectrum in FIG. 3 however is a single beam spectrum of acetone (so labeled) with no UV exposure.

The time dependence of spectral features in FIG. 3 is obvious. The sampling interferometer was not purged, therefore the atmospheric $CO_2$ feature is present in each spectrum at 2349 $cm^{-1}$. Photodecomposition of acetone produces CO with a band origin at 2149 $cm^{-1}$ superimposed upon the acetone band.

The spectral feature with a band origin at 3138 $cm^{-1}$ demonstrates the utility of the invention. This sequence of experiments was undertaken to study the reaction as it occurred in the well known dissociation scheme

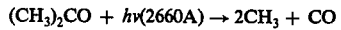
$(CH_3)_2CO + h\nu(2660A) \rightarrow 2CH_3 + CO$

Several unexpected features were observed. The spectral feature at 3138 $cm^{-1}$ which has been tentatively identified as due to ketene absorption, forms after the UV flash, increases in concentration until 3.24 milliseconds, and disappears in the next 0.40 millisecond.

Other spectral features between 2500 and 2800 $cm^{-1}$ appear in emission 40 microseconds after the UV flash. By 1.24 milliseconds this system is absorbing and at 3.64 milliseconds the system is once again emitting.

Figure 4:
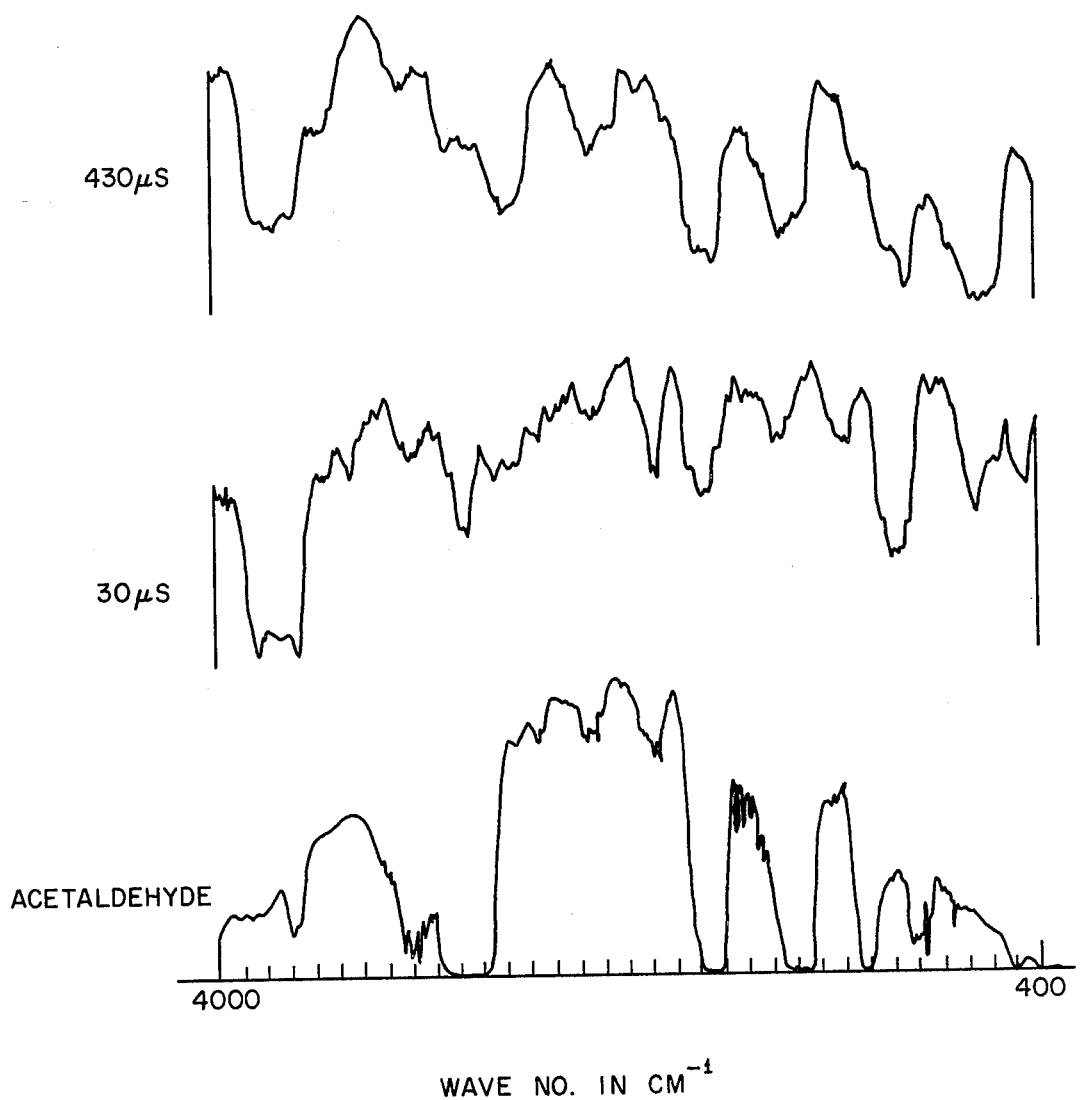
FIG. 4 shows representative spectra obtained by transformation of some synthetic interferograms derived from the photolysis of acetaldehyde.

A similar series of spectra shown in FIG. 4 (compared to the spectrum taken without UV exposure at the bottom of FIG. 4) were derived from acetaldehyde UV photolysis according to the present invention. The very substantial changes occurring between 30 μsec and 430 μsec following UV exposure can readily be observed.

Since certain changes may be made in the above apparatus and process without departing from the scope of the invention herein involved, it is intended that all matter contained in the above description or shown in the accompanying drawing shall be interpreted as illustrative and not in a limiting sense.

```
0001   .MAIN MACRO REV 02
01              ;SPECIAL PROGRAM FOR ARLAN MANTZ
02
03      003500  PGLOC=5500    ;ADDRESS OF PROGRAM ON DISK
04      000005  SML=5         ;SIGNED DEVICE CODE FOR MUL-DIV
05      000001  UMD=1         ;UNSIGNED DEVICE CODE FOR MUL-DIV
06      000017  XABORT=17
07      000340  XDISK=340
08      000341  XATOD=341
09      000342  XPLOT=342
10      000343  XALARM=343
```

```
11      000344 XTTOUT=344
12      000345 XTTIN=345
13      000566 XESCP=566
14      000355 XCMSK=355
15      000367 XDSMS=367
16      000150 XEXEC=150
17      000172 AFINFO=172
18      000176 XKPGM=176
19
20      006276 DREAD=JSR @276
21      006277 DWRITE=JSR @277
22      006273 DWAIT=JSR @273
23
24      000240 FINFS=240          ;FINFO DISK SECTOR ADDRESS
25      000112 FLS=112
26      000065 FLD=65
27      000137 CNT=137
28
29      000200 TEMP=200
30      000201 OTS=201
31      000202 FILE=202
32      000203 DELTA=203
33      000204 P=204
34      000205 LOOPC=205
35      000206 OTFL=206
36      000207 SOTFL=207
37      000210 DISP=210
38      000211 GFW=211
39      000212 NSCN=212
40      000213 DPF=213
41      000214 OFTN=214
42      000215 NSEC=215
43      000216 SUM=216
44      000220 PKV=220
45      000234 LOC=234
46      000222 FIXP=222
47      000223 FOUTP=223
48      000224 FLC=224
49      000225 SFLC=225
50      000226 SBAVG=226
51      000227 FIXLC=227
52      000230 OFDS=230
53      000231 PEAK=231
54      000232 LWBUF=232
55      000233 LRBUF=233
56      000235 WP=235
```

APPENDIX A

```
!0002 ;MAIN
01
02                      ;THE PROGRAM STARTS HERE
03
04
05      000600 .LOC 600
06
07
08 00600 060277 START:  INTDS
09 00601 102000          ADC 0,0
10 00602 040355          STA 0,XCMSK
11 00603 062077          MSKO 0              ;DISABLE ALL INTERRUPTS
12 00604 020431          LDA 0,K3
13 00605 040340          STA 0,XDISK
14 00606 040341          STA 0,XATOD
15 00607 040343          STA 0,XALARM
16 00610 040344          STA 0,XTTOUT
17 00611 040342          STA 0,XPLOT
18 00612 020424          LDA 0,ESCP
19 00613 040345          STA 0,XTTIN
20 00614 060177          INTEN
21
22 00615 020414          LDA 0,NXT          ;ADDRESS OF NEXT SECTOR OF PROGRAM
```

```
23 00616 024414          LDA 1,NXTC       ;ITS CORE LOCATION
24 00617 006276          DREAD
25 00620 006273          DWAIT
26 00621 020412          LDA 0,KRB        ;SET UP PAGE ZERO LINKS
27 00622 040233          STA 0,LRBUF
28 00623 020411          LDA 0,KWB
29 00624 040232          STA 0,LWBUF
30 00625 020137          LDA 0,CNT
31 00626 101005          MOV 0,0,SNR      ;CHECK FOR A PARAMETER ERROR
32 00627 002410          JMP @SERR
33 00630 000410          JMP STRT0
34 00631 005501 NXT:     PGLOC+1
35 00632 001200 NXTC:    1200
36 00633 002000 KRB:     RBUF
37 00634 002400 KWB:     WBUF
38 00635 000003 K3:      3
39 00636 000566 ESCP:    566
40 00637 001030 SERR:    ERR
   !0003 .MAIN
01
02 00640 020137 STRT0:   LDA 0,CNT        ;# OF FILES TO CREATE
03 00641 040205          STA 0,LOOPC      ;LOOP COUNTER
04
05 00642 020112          LDA 0,FLS
06 00643 004576          JSR FINC         ;CALCULATE FINFO ADDRESSES
07 00644 000564          JMP ERR          ;ADDRESS OF RBUF
08 00645 024233          LDA 1,LRBUF      ;ADDRESS OF RBUF
09 00646 050200          STA 2,TEMP
10 00647 006276          DREAD
11 00650 006273          DWAIT
12 00651 024233          LDA 1,LRBUF
13 00652 030200          LDA 2,TEMP
14 00653 133000          ADD 1,2
15 00654 021000          LDA 0,0,2        ;GENERAL WORD FLAG
16 00655 040211          STA 0,GFW
17 00656 025001          LDA 1,1,2
18 00657 044212          STA 1,NSCN
19 00660 024555          LDA 1,K3777
20 00661 107400          AND 0,1
21 00662 044215          STA 1,NSEC       ;NUMBER OF SECTORS PER FILE
22 00663 024554          LDA 1,K40K
23 00664 107400          AND 0,1
24 00665 044213          STA 1,DPF        ;DOUBLE PRECISION FLAG
25
26 00666 020176          LDA 0,XKPGM      ;ADDRESS OF FIRST FREE DISC SEC
27 00667 024215          LDA 1,NSEC       ;# OF SECS PER FILE
28 00670 030065          LDA 2,FLD        ;FIRST OUTPUT FILE #
29 00671 151005          MOV 2,2,SNR
30 00672 000405          JMP LP           ;FLD=0
31 00673 150400          NEG 2,2          ;MAKE INTO A COUNTER
32 00674 123000          ADD 1,0
33 00675 151404          INC 2,2,SZR
34 00676 000776          JMP .-2
35 00677 040206 LP:      STA 0,OTFL       ;OUTPUT FILE LOCATION
36 00700 040207          STA 0,SOTFL      ;SAVED COPY
37
38 00701 102400          SUB 0,0
39 00702 040210          STA 0,DISP       ;INITIALIZE STARTING DISPLACEMENT
40
   !0004 .MAIN
01 00703 040202 LPZ:     STA 0,FILE
02 00704 040203          STA 0,DELTA
03 00705 020210          LDA 0,DISP       ;STARTING DISPLACEMENT
04 00706 030213          LDA 2,DPF        ;GET FILE TYPE
05 00707 126520          SUBZL 1,1        ;=1
06 00710 151004          MOV 2,2,SZR
07 00711 103000          ADD 0,0          ;2X DISP
08 00712 151004          MOV 2,2,SZR
09 00713 127000          ADD 1,1          ;2X INCREMENT = 2
10
11 00714 030137          LDA 2,CNT
12 00715 150400          NEG 2,2          ;CONVERT INTO A COUNTER
13 00716 034522          LDA 3,LTAB       ;ADDRESS OF POINTER TABLE
14
```

```
15 00717 041400 LNT0:    STA 0,0,3        ;CREATE POINTERS
16 00720 175400         INC 3,3
17 00721 123000         ADD 1,0
18 00722 151404         INC 2,2,SZR
19 00723 000774         JMP LNT0
20
21 00724 020176 LP1:    LDA 0,XKPGN      ;FIRST FREE SECTOR
22 00725 024203         LDA 1,DELTA      ;DISP INTO A FILE (SECTORS)
23 00726 123000         ADD 1,0
24 00727 030112         LDA 2,FLS        ;ADDRESS OF SOURCE FILE
25 00730 024202         LDA 1,FILE       ;FILE DISP FROM FLS
26 00731 133005         ADD 1,2,SNR
27 00732 000406         JMP +6
28 00733 024215         LDA 1,NSEC       ;# OF SECTORS PER FILE
29 00734 150400         NEG 2,2          ;MAKE INTO A COUNTER
30 00735 123000         ADD 1,0          ;COMPUTE ADDRESS OF BUFFER
31 00736 151404         INC 2,2,SZR
32 00737 000776         JMP -2
33 00740 024233         LDA 1,LRBUF      ;ADDRESS FOR CORE BUFFER
34 00741 006276         DREAD
35 00742 006273         DWAIT

!0005 MAIN -
01
02 00743 034475 LNT1:   LDA 3,LTAB
03 00744 020202         LDA 0,FILE
04 00745 117000         ADD 0,3
05 00746 054201         STA 3,@TS        ;SAVE TABLE POINTER
06 00747 025400         LDA 1,0,3        ;STARTING VALUE FOR P
07 00750 044204         STA 1,P
08
09 00751 020463 LP2:    LDA 0,K377       ;SECTOR LENGTH - 1
10 00752 122433         SUBZ# 1,0,SNC    ;SKIP IF AC1 <= AC0
11 00753 000424         JMP LP3          ;P > SECTOR LENGTH - 1
12 00754 030233         LDA 2,LRBUF
13 00755 133000         ADD 1,2
14 00756 034232         LDA 3,LWBUF
15 00757 137000         ADD 1,3
16 00760 021000         LDA 0,0,2
17 00761 041400         STA 0,0,3        ;MOVE ENTRY
18 00762 024213         LDA 1,DPF
19 00763 125005         MOV 1,1,SNR
20 00764 000403         JMP LP2A         ;ENTRY IS SP
21 00765 021001         LDA 0,1,2        ;GET OTHER PART OF DP ENTRY
22 00766 041401         STA 0,1,3
23 00767 020137 LP2A:   LDA 0,CNT
24 00770 024204         LDA 1,P
25 00771 030213         LDA 2,DPF        ;GET FILE TYPE
26 00772 107000         ADD 0,1
27 00773 151004         MOV 2,2,SZR
28 00774 107000         ADD 0,1          ;ADD TWICE FOR DP FILES
29 00775 044204         STA 1,P
30 00776 000753         JMP LP2

!0006 MAIN
01
02 00777 020436 LP3:    LDA 0,K400
03 01000 105400         SUB 0,1          ;COMPUTE LENGTH PAST END
04 01001 046201         STA 1,@TS        ;UPDATE TABLE POINTER
05 01002 010202         ISZ FILE         ;GO TO NEXT FILE
06 01003 030202         LDA 2,FILE       ;DISPLACEMENT FROM FLS
07 01004 024137         LDA 1,CNT
08 01005 146424         SUBZ 2,1,SZR
09 01006 000716         JMP LP1          ;FILE <> CNT
10 01007 044202         STA 1,FILE       ;RESET BACK TO 0
11 01010 010203         ISZ DELTA        ;GO TO NEXT SECTOR INTO THE FILES
12
13 01011 020205         LDA 0,OTFL       ;OUTPUT FILE ADDRESS
14 01012 010205         ISZ OTFL
15 01013 024232         LDA 1,LWBUF      ;CORE ADDRESS OF BUFFER
16 01014 006277         DWRITE
17 01015 006273         DWAIT
18
19 01016 020203         LDA 0,DELTA
20 01017 101400         INC 0,0
21 01020 024215         LDA 1,NSEC
```

```
22 01021 105432            SUBZ# 0,1,SZC      ;SKIP IF DELTA +1 > NSEC
23 01022 000702            JMP LP1            ;KEEP GOING
24
25 01023 102400            SUB 0,0
26 01024 010210            ISZ DISP
27 01025 014205            DSZ LOOPC
28 01026 000655            JMP LP2            ;DO ANOTHER FILE
29 01027 000433            JMP FIXUP          ;NOW CLEAN UP THE FILES
30
31
32 01030 020403 ERR:       LDA 0,ERRC         ;=?
33 01031 061111            DOAS 0,TTO
34 01032 000017            JMP XABORT
35 01033 000077 ERRC:      77
36
37 01034 000377 K377:      377
38 01035 000400 K400:      400
39 01036 003777 K3777:     3777
40 01037 040000 K40K:      40000
41 01040 001600 LTAB:      TABLE
;0007  MAIN
01
02
03                         ;INPUT AC0=FILE #
04                         ;
05                         ;OUTPUT AC0= DISK ADDRESS OF FINFO SECTOR
06                         ;       AC2= INDEX INTO FINFO SECTOR
07                         ;
08                         ;RETURN +1 = ERROR
09                         ;       +2 = NORMAL
10
11 01041 054415 FINC:      STA 3,FINCR
12 01042 103120            ADDZL 0,0          ;4X
13 01043 034414            LDA 3,FINLH        ;=177400
14 01044 117700            ANDS 0,3           ;AC3 = SECTOR DISPLACEMENT
15 01045 030413            LDA 2,FINRH        ;=377
16 01046 113400            AND 0,2            ;=INDEX INTO SECTOR
17 01047 020412            LDA 0,FINCT        ;FINFO SECTOR LIMIT
18 01050 162433            SUBZ# 3,0,SNC
19 01051 002405            JMP @FINCR         ;ADDRESSING ERROR
20 01052 020172            LDA 0,AFINFO       ;ADDRESS OF FINFO DISK SECTOR
21 01053 163000            ADD 3,0
22 01054 010402            ISZ FINCR          ;TAKE THE GOOD RETURN
23 01055 002401            JMP @FINCR
24
25 01056 000000 FINCR:     0
26 01057 177400 FINLH:     177400
27 01060 000377 FINRH:     000377
28 01061 000003 FINCT:     3
;0008  MAIN
01 01062 020137 FIXUP:     LDA 0,CNT          ;FIND THE PEAK LOCATIONS AND ALSO
02 01063 040227            STA 0,FIXLC        ;CALCULATE THE AVERAGE BACKGROUND
03 01064 102400            SUB 0,0
04 01065 040210            STA 0,DISP
05 01066 020065            LDA 0,FLD          ;VALUE AND SUBTRACT IT FROM THE FILES
06 01067 040230            STA 0,OFDS
07 01070 020215            LDA 0,NSEC
08 01071 101300            MOVS 0,0           ;FIND THE # OF POINTS (ASSUME <=64K SF
09 01072 024213            LDA 1,DPF          ;CHECK FILE TYPE
10 01073 125004            MOV 1,1,SZR
11 01074 101220            MOVZR 0,0          ;FILE IS DP, DIVIDE BY TWO TO GET POINT
12 01075 024137            LDA 1,CNT          ;# OF FILES
13 01076 122400            SUB 1,0
14 01077 040225            STA 0,SFLC         ;# OF POINTS TO PROCESS PER FILE
15
16 01100 102400 FIX:       SUB 0,0            ;INITIALIZE FOR A PASS THROUGH A FILE
17 01101 040220            STA 0,PKV          ;CLEAR THE PEAK VALUE
18 01102 040221            STA 0,PKV+1
19 01103 040216            STA 0,SUM          ;CLEAR THE RUNNING SUM
20 01104 040217            STA 0,SUM+1
21 01105 040234            STA 0,LOC          ;PEAK LOCATION INDICATOR
22 01106 024225            LDA 1,SFLC         ;# OF POINTS/FILE
23 01107 044224            STA 1,FLC
24 01110 024207            LDA 1,SOTFL        ;DISK ADDRESS OF OUTPUT FILE
```

```
25 01111 044205           STA 1,OTFL
26 01112 030213           LDA 2,DPF        ;CHECK FILE TYPE
27 01113 034210           LDA 3,DISP       ;STARTING DISPLACEMENT
28 01114 151004           MOV 2,2,SZR
29 01115 175120           MOVZL 3,3        ;FILE IS DP, MUST 2X
30 01116 024233           LDA 1,LRBUF      ;ADDRESS OF INPUT BUFFER
31 01117 137000           ADD 1,3
32 01120 054222           STA 3,FIXP       ;STARTING ADDRESS IN BUFFER
33 01121 000403           JMP FIXG
;0009 .MAIN
01
02 01122 024233 FIX .:    LDA 1,LRBUF      ;INTO RBUF
03 01123 044222           STA 1,FIXP       ;POINTER TO ENTRY IN BUFFER
04 01124 020206 FIXG:     LDA 0,OTFL       ;INPUT SECTOR ADDRESS
05 01125 006276           DREAD
06 01126 006273           DWAIT
07
08
09 01127 034222 FIX :     LDA 3,FIXP       ;POINTER INTO BUFFER
10 01130 030213           LDA 2,DPF        ;FLAG FOR FILE TYPE
11 01131 151005           MOV 2,2,SNR
12 01132 000405           JMP FIX0         ;FILE IS SP
13
14 01133 021400           LDA 0,0,3        ;FILE IS DP
15 01134 025401           LDA 1,1,3        ;LSH OF ENTRY
16 01135 010222           ISZ FIXP
17 01136 000405           JMP FIX1
18
19 01137 025400 FIX0:     LDA 1,0,3        ;FILE IS SP
20 01140 102400           SUB 0,0          ;FAKE A DP FILE TYPE
21 01141 125132           MOVZL# 1,1,SZC
22 01142 100000           COM 0,0          ;FUDGE MSH OF ENTRY
23 01143 010222 FIX1:     ISZ FIXP
24
25
26 01144 030216           LDA 2,SUM        ;MSH OF RUNNING SUM
27 01145 034217           LDA 3,SUM+1      ;LSH OF RUNNING SUM
28 01146 137022           ADDZ 1,3,SZC     ;DO A DP ADD
29 01147 151400           INC 2,2
30 01150 113000           ADD 0,2
31 01151 050216           STA 2,SUM        ;SAVE SUM
32 01152 054217           STA 3,SUM+1
;0010 .MAIN
01
02 01153 101133           MOVZL# 0,0,SNC   ;CHECK SIGN OF DP NUMBER
03 01154 000404           JMP FIX2         ;IS +
04 01155 124405           NEG 1,1,SNR      ;IS - MAKE +
05 01156 100401           NEG 0,0,SKP
06 01157 100000           COM 0,0          ;NOW HAVE ABS VALUE OF #
07
08 01160 030220 FIX2:     LDA 2,PKV        ;PEAK VALUE
09 01161 034221           LDA 3,PKV+1
10 01162 112433           SUBZ# 0,2,SNC    ;SKIP IF AC0 (NEW) <= AC2 (OLD)
11 01163 000405           JMP FIX3         ;AC0 > AC2 HAVE A NEW LOCATION
12 01164 112434           SUBZ# 0,2,SZR
13 01165 000407           JMP FIX4         ;AC0 <> AC2 GET NEXT POINT
14 01166 136432           SUBZ# 1,3,SZC    ;EQUAL, CHECK LSH, SKIP IF AC1 > AC3
15 01167 000405           JMP FIX4         ;NO, AC1 <= AC3, GET NEXT POINT
16
17 01170 040220 FIX3:     STA 0,PKV        ;SAVE NEW PEAK VALUE
18 01171 044221           STA 1,PKV+1
19 01172 020234           LDA 0,LOC
20 01173 040231           STA 0,PEAK       ;SAVE ITS LOCATION
21
22 01174 010234 FIX4:     ISZ LOC
23 01175 020222           LDA 0,FIXP       ;SEE IF PAST THE BUFFER
24 01176 024636           LDA 1,K377
25 01177 107405           AND 0,1,SNR
26 01200 000404           JMP FIX5         ;NEED NEXT SECTOR
27 01201 014224           DSZ FLC          ;JUST COUNT THE POINT PROCESSED
28 01202 000725           JMP FIX          ;CONTINUE WITH PRESENT BUFFER
29 01203 000404           JMP FIXE         ;NOW UPDATE FILES
30
31 01204 010205 FIX5:     ISZ OTFL         ;POINT TO THE NEXT FILE SECTOR
```

```
32 01205 014224            DSZ FLC              ;COUNT THE POINT PROCESSED
33 01206 000714            JMP FIX              ;READ IN THE NEW BUFFER
34
35 01207 020216  FIXE:     LDA 0,SUM            ;HERE WHEN DONE WITH FIRST PASS
36 01210 024217            LDA 1,SUM+1
37 01211 030225            LDA 2,SFLC           ;CALCULATE AVERAGE VALUE
38 01212 006475            JSR @FXDIV
39 01213 044226            STA 1,SBAVG          ;SAVE THE QUOTIENT
40
41 01214 004527            JSR CLR              ;INIT THE OUTPUT BUFFER
42 01215 020225            LDA 0,SFLC           ;INIT FOR FILE CORRECTION
43 01216 040224            STA 0,FLC
44 01217 020207            LDA 0,SOTFL
45 01220 040223            STA 0,FOUTP          ;INIT OUTPUT FILE ADDRESS
46 01221 040205            STA 0,OTFL           ;UPDATE FILE POINTER
47 01222 020232            LDA 0,LWBUF          ;START OF OUTPUT BUFFER
48 01223 040517            STA 0,PUTL           ;INIT OUTPUT ROUTINE POINTER
49 01224 030213            LDA 2,DPF            ;CHECK FILE TYPE
50 01225 020210            LDA 0,DISP           ;INITIAL DISPLACEMENT
51 01226 151004            MOV 2,2,SZR
52 01227 101120            MOVZL 0,0            ;FILE IS DP, MUST 2X
53 01230 000402            JMP FIXA0
54
55 01231 102400  FIXE0:    SUB 0,0
56 01232 040222  FIXA0:    STA 0,FIXP           ;INIT INDEX INTO BUFFER
57 01233 020205            LDA 0,OTFL
58 01234 024233            LDA 1,LRBUF
59 01235 006276            DREAD
60 01236 006273            DWAIT
   0011  MAIN
01
02 01237 034222  FIXE1:    LDA 3,FIXP           ;INDEX INTO BUFFERS
03 01240 030233            LDA 2,LRBUF
04 01241 173000            ADD 3,2               ;AC2 = ADDRESS OF ENTRY IN RBUF
05 01242 034226            LDA 3,SBAVG          ;AVERAGE VALUE FOR ENTRY
06
07 01243 024213            LDA 1,DPF            ;CHECK FILE TYPE
08 01244 125005            MOV 1,1,SNR
09 01245 000434            JMP FIXE2            ;FILE IS SP
10 01246 021000            LDA 0,0,2            ;FILE IS DP
11 01247 025001            LDA 1,1,2
12
13 01250 152400            SUB 2,2              ;PREPARE TO FAKE A DP #
14 01251 175132            MOVZL# 3,3,SZC       ;CHECK SIGN OF SBAVG
15 01252 150000            COM 2,2              ;IS -, CORRECT MSH
16
17 01253 166422            SUBZ 3,1,SZC         ;DP SUB; C(0,1) - C(2,3)
18 01254 142401            SUB 2,0,SKP
19 01255 142000            ADC 2,0
20
21 01256 004434            JSR PUT              ;OUTPUT TO BUFFER
22 01257 010222            ISZ FIXP
23
24 01260 010222  FIXE3:    ISZ FIXP
25 01261 020222            LDA 0,FIXP           ;CHECK FOR NEW BUFFER BEING NEEDED
26 01262 024426            LDA 1,FX377
27 01263 107404            AND 0,1,SZR
28 01264 000406            JMP FIXE4            ;NO CONTINUE
29
30 01265 010205            ISZ OTFL             ;POINT TO NEXT SECTOR IN FILE
31
32 01266 014224            DSZ FLC              ;COUNT A POINT BEING PROCESSED
33 01267 000742            JMP FIXE0            ;GO GET A NEW FILE SECTOR
34 01270 063077            HALT                 ;SHOULD NEVER GET HERE
35 01271 002415            JMP @FERR            ;JUST FOR PROTECTION
36
37 01272 014224  FIXE4:    DSZ FLC  ;COUNT A POINT PROCESSED
38 01273 000744            JMP FIXE1            ;DO MORE
39
40 01274 020223            LDA 0,FOUTP          ;OUTPUT LAST BUFFER
41 01275 024232            LDA 1,LWBUF
42 01276 006277            DWRITE
43 01277 006273            DWAIT
44 01300 000453            JMP FINUP            ;UPDATE FINFO
```

```
!0012  MAIN
01
02  01301  021000  FIXE2:    LDA 0,0,2         ;HERE ON A SP FILE
03  01302  162400            SUB 3,0
04  01303  004407            JSR PUT           ;OUTPUT TO BUFFER
05  01304  000654            JMP FIX3
06
07  01305  177400  KM400:    -400
08  01306  001030  FERR:     ERR
09  01307  001426  FXDIV:    .DIV
10  01310  000377  FX377:    377
11  01311  001041  FXFNO:    FINO
12
13
14
15  01312  054427  PUT:      STA 3,PUTR
16  01313  034213            LDA 3,OFF         ;GET FILE TYPE
17  01314  030426            LDA 2,PUTL        ;POINTER INTO FILE
18  01315  175004            MOV 3,3,SZR       ;CHECK FILE TYPE
19  01316  000403            JMP PUT0          ;FILE IS DP
20  01317  045000            STA 1,0,2         ;FILE IS SP
21  01320  000404            JMP PUT1
22
23  01321  041000  PUT0:     STA 0,0,2
24  01322  045001            STA 1,1,2
25  01323  151400            INC 2,2
26  01324  151400  PUT1:     INC 2,2
27  01325  050415            STA 2,PUTL        ;UPDATE THE POINTER
28  01326  024762            LDA 1,FX377
29  01327  133404            AND 1,2,SZR       ;CHECK FOR BUFFER BEING FILLED
30  01330  002411            JMP @PUTR         ;ROOM LEFT
31
32  01331  024232            LDA 1,LWBUF       ;DUMP BUFFER OUT
33  01332  044410            STA 1,PUTL        ;RESET POINTER AS WE GO
34  01333  020223            LDA 0,FOUTP       ;ADDRESS FOR OUTPUT FILE SECTOR
35  01334  005277            DWRITE
36  01335  005273            DWAIT
37  01336  010223            ISZ FOUTP         ;INCREMENT POINTER FOR NEXT TIME
38  01337  004404            JSR CLR           ;INIT BUFFER TO ZEROS
39  01340  002401            JMP @PUTR         ;NOW RETURN
40  01341  000000  PUTR:     0
41  01342  000000  PUTL:     0
42
43  01343  030232  CLR:      LDA 2,LWBUF       ;ADDRESS OF OUTPUT BUFFER
44  01344  024741            LDA 1,KM400       ;=-400
45  01345  102400            SUB 0,0
46  01346  041000            STA 0,0,2
47  01347  151400            INC 2,2
48  01350  125404            INC 1,1,SZR
49  01351  000775            JMP -3
50  01352  001400            JMP 0,3

!0013  MAIN
01
02  01353  020230  FINUP:    LDA 0,OFDS        ;OUTPUT FILE #
03  01354  006735            JSR @FXFNO        ;GET FINFO ADDRESS
04  01355  002731            JMP @FERR
05  01356  040203            STA 0,DELTA       ;USE AS A TEMP
06  01357  024233            LDA 1,LRBUF       ;AC0 = DISK ADDRESS
07  01360  133000            ADD 1,2
08  01361  050222            STA 2,FIXP        ;TEMP POINTER INTO BUFFER
09  01362  006276            DREAD
10  01363  005273            DWAIT
11
12  01364  030222            LDA 2,FIXP
13  01365  020211            LDA 0,GFW
14  01366  041000            STA 0,0,2
15  01367  020212            LDA 0,NSCN
16  01370  041001            STA 0,1,2
17  01371  102400            SUB 0,0           ;NSCL=0
18  01372  041002            STA 0,2,2
19  01373  020231            LDA 0,PEAK
20  01374  041003            STA 0,3,2
21
22  01375  020203            LDA 0,DELTA
```

```
23 01376 024233           LDA 1,LRBUF
24 01377 005277           DWRITE
25 01400 005273           DWAIT
26
27 01401 020207           LDA 0,SOTFL
28 01402 024215           LDA 1,NSEC      ;LENGTH OF A FILE
29 01403 123000           ADD 1,0
30 01404 040207           STA 0,SOTFL     ;ADDRESS OF NEXT FILE
31 01405 010230           ISZ OFDS        ;NEXT FILE NUMBER
32 01406 010210           ISZ DISP        ;MUST INCREASE DISPLACEMENT BY 1
33
34 01407 014227           DSZ FIXLC
35 01410 002402           JMP @L FIX      ;DO ANOTHER FILE
36 01411 000150           JMP XEXEC
37
38 01412 001100   L FIX:  .FIX

;0014  MAIN
01
02                ;SIGNED HARDWARE MULTIPLY
03
04 01413 056005   MULS:   DOB 1,SML
05 01414 073305           DOCP 2,SML      ;MULTIPLY AC1 BY AC2
06 01415 060000           NIO 0
07 01416 060300           NIOP 0
08 01417 065405           DIB 1,SML       ;LSH
09 01420 050405           DIA 0,SML       ;MSH
10 01421 101133           MOVZL# 0,0,SNC  ;SHIFT RIGHT 1 BIT
11 01422 101221           MOVZR 0,0,SKP   ;FILL WITH A ZERO = +
12 01423 101240           MOVR 0,0        ;FILL WITH A ONE = -
13 01424 125200           MOVR 1,1        ;RESULT IS A SIGNED 30 BIT #
14 01425 001400           JMP 0,3         ;RIGHT ADJUSTED IN AC0,AC1
15
16
17                ;UNSIGNED HARDWARE DIVIDE
18
19 01426 142432   DIV:    SUBZ# 2,0,SZC
20 01427 000411           JMP DIV0        ;OVERFLOW OR ILLEGAL
21 01430 061001           DOA 0,UMD       ;MSH
22 01431 065001           DOB 1,UMD       ;LSH
23 01432 073101           DOCS 2,UMD      ;DIVISOR
24 01433 060000           NIO 0
25 01434 060300           NIOP 0
26 01435 050401           DIA 0,UMD       ;REMAINDER
27 01436 054401           DIB 1,UMD       ;QUOTIENT
28 01437 001400           JMP 0,3
29 01440 102400   DIV0:   SUB 0,0
30 01441 125420           SUBZ 1,1        ;RETURN A ZERO
31 01442 001400           JMP 0,3
32
33
34
35         001600        .LOC 1600
36 01600 000000   TABLE:  0
37
38         002000        .LOC 2000
39
40 02000 000400   RBUF:   .BLK 400
41
42 02400 000400   WBUF:   .BLK 400
43
44 03000 000000   FOO:    0
45
46                        .END
   0015  MAIN
```

| | | | | | | | |
|---|---|---|---|---|---|---|---|
| AFINF | 000172 | 1/17 | 7/20 | | | | |
| CLR | 001343 | 10/41 | 12/38 | 12/43 | | | |
| CNT | 000137 | 1/27 | 2/30 | 3/02 | 4/11 | 5/23 | 6/07 | 8/01 |
| | | 8/12 | | | | | | |
| DELTA | 000203 | 1/32 | 4/02 | 4/22 | 6/11 | 6/19 | 13/05 | 13/22 |
| DISP | 000210 | 1/37 | 3/39 | 4/03 | 6/26 | 8/04 | 8/27 | 10/50 |
| | | 13/32 | | | | | | |
| DPF | 000213 | 1/40 | 3/24 | 4/04 | 5/18 | 5/25 | 8/09 | 8/26 |
| | | 9/10 | 10/49 | 11/07 | 12/16 | | | |

| | | | | | | | | |
|---|---|---|---|---|---|---|---|---|
| DREAD | 005276 | 1/20 | 2/24 | 3/10 | 4/34 | 9/05 | 10/59 | 13/09 |
| DWAIT | 005273 | 1/22 | 2/25 | 3/11 | 4/35 | 6/17 | 9/06 | 10/60 |
| | | 11/43 | 12/36 | 13/10 | 13/25 | | | |
| DWRIT | 005277 | 1/21 | 6/16 | 11/42 | 12/35 | 13/24 | | |
| ERR | 001030 | 2/40 | 3/07 | 6/32 | 12/08 | | | |
| ERRC | 001033 | 6/32 | 6/35 | | | | | |
| ESCP | 000535 | 2/18 | 2/39 | | | | | |
| FERR | 001305 | 11/35 | 12/08 | 13/04 | | | | |
| FILE | 000202 | 1/31 | 4/01 | 4/25 | 5/03 | 6/05 | 6/06 | 6/10 |
| FINC | 001041 | 3/06 | 7/11 | 12/11 | | | | |
| FINCR | 001056 | 7/11 | 7/19 | 7/22 | 7/23 | 7/25 | | |
| FINCT | 001061 | 7/17 | 7/28 | | | | | |
| FINFS | 000240 | 1/24 | | | | | | |
| FINLH | 001057 | 7/13 | 7/26 | | | | | |
| FINRH | 001060 | 7/15 | 7/27 | | | | | |
| FINUP | 001353 | 11/44 | 13/02 | | | | | |
| FIX0 | 001137 | 9/12 | 9/19 | | | | | |
| FIX1 | 001143 | 9/17 | 9/23 | | | | | |
| FIX2 | 001160 | 10/03 | 10/08 | | | | | |
| FIX3 | 001170 | 10/11 | 10/17 | 12/05 | | | | |
| FIX4 | 001174 | 10/13 | 10/15 | 10/22 | | | | |
| FIX5 | 001204 | 10/26 | 10/31 | | | | | |
| FIXA0 | 001232 | 10/53 | 10/56 | | | | | |
| FIXE | 001207 | 10/29 | 10/35 | | | | | |
| FIXE0 | 001231 | 10/55 | 11/33 | | | | | |
| FIXE1 | 001237 | 11/02 | 11/38 | | | | | |
| FIXE2 | 001301 | 11/09 | 12/02 | | | | | |
| FIXE3 | 001260 | 11/24 | | | | | | |
| FIXE4 | 001272 | 11/28 | 11/37 | | | | | |
| FIXG | 001124 | 8/33 | 9/04 | | | | | |
| FIXLC | 000227 | 1/51 | 8/02 | 13/34 | | | | |
| FIXP | 000222 | 1/46 | 8/32 | 9/03 | 9/09 | 9/16 | 9/23 | 10/23 |
| | | 10/56 | 11/02 | 11/22 | 11/24 | 11/25 | 13/08 | 13/12 |
| FIXUP | 001052 | 6/29 | 8/01 | | | | | |
| FIX | 001127 | 9/09 | 10/28 | | | | | |
| FIX | 001122 | 9/02 | 10/33 | | | | | |
| FLC | 000224 | 1/48 | 8/23 | 10/27 | 10/32 | 10/43 | 11/32 | 11/37 |
| FLD | 000065 | 1/26 | 3/28 | 8/05 | | | | |
| FLS | 000112 | 1/25 | 3/05 | 4/24 | | | | |
| FOO | 003000 | 14/44 | | | | | | |
| FOUTP | 000223 | 1/47 | 10/45 | 11/40 | 12/34 | 12/37 | | |
| FX377 | 001310 | 11/26 | 12/10 | 12/28 | | | | |
| FXDIV | 001307 | 10/38 | 12/09 | | | | | |
| FXFNC | 001311 | 12/11 | 13/03 | | | | | |
| GFW | 000211 | 1/38 | 3/16 | 13/13 | | | | |
| K3 | 000635 | 2/12 | 2/38 | | | | | |
| K377 | 001034 | 5/09 | 6/37 | 10/24 | | | | |
| K3777 | 001036 | 3/19 | 6/39 | | | | | |
| K400 | 001035 | 6/02 | 6/38 | | | | | |
| K40K | 001037 | 3/22 | 6/40 | | | | | |
| 0016 . MAIN | | | | | | | | |
| KM400 | 001305 | 12/07 | 12/44 | | | | | |
| KRB | 000633 | 2/26 | 2/36 | | | | | |
| KWB | 000534 | 2/28 | 2/37 | | | | | |
| LNT0 | 000717 | 4/15 | 4/19 | | | | | |
| LNT1 | 000743 | 5/02 | | | | | | |
| LOC | 000234 | 1/45 | 8/21 | 10/19 | 10/22 | | | |
| LOOPC | 000205 | 1/34 | 3/03 | 6/27 | | | | |
| LP1 | 000724 | 4/21 | 5/09 | 6/23 | | | | |
| LP2 | 000751 | 5/09 | 5/30 | | | | | |
| LP2A | 000767 | 5/20 | 5/23 | | | | | |
| LP3 | 000777 | 5/11 | 6/02 | | | | | |
| LPZ | 000703 | 4/01 | 6/28 | | | | | |
| LP. | 000677 | 3/30 | 3/35 | | | | | |
| LRBUF | 000233 | 1/55 | 2/27 | 3/08 | 3/12 | 4/33 | 5/12 | 8/30 |
| | | 9/02 | 10/58 | 11/03 | 13/06 | 13/23 | | |
| LTAB | 001040 | 4/13 | 5/02 | 6/41 | | | | |
| LWBUF | 000232 | 1/54 | 2/29 | 5/14 | 6/15 | 10/47 | 11/41 | 12/32 |
| | | 12/43 | | | | | | |
| L FIX | 001413 | 13/35 | 13/38 | | | | | |
| NSCN | 000212 | 1/39 | 3/18 | 13/15 | | | | |
| NSEC | 000215 | 1/42 | 3/21 | 3/27 | 4/28 | 6/21 | 8/07 | 13/28 |
| NXT | 000631 | 2/22 | 2/34 | | | | | |

```
NXTC  000532    2/23   2/35
OFDS  000230    1/52   8/05   13/02  13/31
OFTN  000214    1/41
OTFL  000205    1/35   3/35   6/13   6/14   8/25   9/04   10/31
                10/46  10/57  11/30
OTS   000201    1/30   5/05   6/04
P     000204    1/33   5/07   5/24   5/29
PEAK  000231    1/53   10/20  13/19
PGLOC 000500    1/03   2/34
PKV   000220    1/44   8/17   8/18   10/08  10/09  10/17  10/18
PUT   001312    11/21  12/04  12/15
PUT0  001321    12/19  12/23
PUT1  001324    12/21  12/25
PUTL  001342    10/48  12/17  12/27  12/33  12/41
PUTR  001341    12/15  12/30  12/39  12/40
RBUF  002000    2/36   14/40
SBAVG 000226    1/50   10/39  11/05
SERR  000537    2/32   2/40
SFLC  000225    1/49   8/14   8/22   10/37  10/42
SM    000005    1/04   14/04  14/05  14/08  14/09
SOTFL 000207    1/36   3/36   8/24   10/44  13/27  13/30
START 000500    2/08
STRT0 000540    2/33   3/02
SUM   000216    1/43   8/19   8/20   9/25   9/27   9/31   9/32
                10/35  10/36
TABLE 001600    6/41   14/36
TEMP  000200    1/29   3/09   3/13
UNO   000001    1/05   14/21  14/22  14/23  14/25  14/27
WBUF  002400    2/37   14/42
WP    000235    1/56
XABOR 000017    1/06   6/34
XALAR 000343    1/10   2/15
XATOD 000341    1/08   2/14
XCHSK 000355    1/14   2/10
XDISK 000340    1/07   2/13
XDSMS 000367    1/15

0017  MAIN

XESCP 000556    1/13
XEXEC 000150    1/16   13/36
XKPGM 000176    1/18   3/26   4/21
XPLOT 000342    1/09   2/17
XTTIN 000345    1/12   2/19
XTTOU 000344    1/11   2/16
DIV   001426    12/09  14/19
DIV0  001440    14/20  14/29
FIX   001100    8/16   13/38
MULS  001413    14/04
```

What is claimed is:

1. A system for resolving a data sequence derived from a time-varying signal-generating phenomenon, said system comprising, in combination:
   means for repetitively initiating said phenomenon;
   means for detecting signals derived from said phenomenon during the course thereof;
   means for repetitively convolving said signals with a transformation;
   means for establishing the temporal relation between initiation of said phenomenon and convolution of said signals so that the repetitive convolution produces an ordered set of first interferograms in which the sequence of the phenomenon and the convolution is temporally shifted in successive increments with respect to one another;
   means for selecting from each interferogram of said set, a data moiety corresponding to a temporal resolution element occurring at a fixed position in time following said initiation during the course of said interferogram; and
   means for combining in a sequence according to the order of said set each of said data moieties so as to synthesize a second interferogram representing the convolution with said transformation of the signals from said phenomenon only at said fixed time position.

2. A system as defined in claim 1 including means for inversely transforming said second interferogram so as to reconstitute data representing said signals occurring during said resolution element as said fixed time position.

3. A system as defined in claim 1 wherein said means for convolving comprises an fast Fourier scanning interferometer.

4. A system as defined in claim 1 wherein said means for establishing the temporal relation between initiation and convolution comprises:
   clock means for producing an electrical pulse train;
   means for controlling said means for convolving in accordance with the timing of said pulse train;
   means for controlling said means for repetitively initiating in accordance with the timing of said pulse train; and means for delaying control of said convolution and said initiation with respect to one another.

5. A system as defined in claim 4 wherein said means for convolving and said clock means respectively comprise scanning interferometers coupled to one another to scan together.

6. A system as defined in claim 4 wherein said means for delaying comprises a first settable electrical counter.

7. A system as defined in claim 6 wherein said means for sampling is controlled in accordance with the timing of said pulse train.

8. A system as defined in claim 7 including means for selectively delaying control of said means for sampling.

9. A system as defined in claim 6 wherein said means for combining comprises said computer.

10. A system as defined in claim 4 wherein a sample-and-hold means for sampling said interferogram and analog-to-digital conversion means for converting the samples of said interferogram to digital form.

11. A system as defined in claim 1 wherein said means for selecting a digital data moieties comprises a digital computer.

12. Method of resolving a data sequence derived from a time-varying signal-generating phenomenon, said method comprising the steps of:

repetitively initiating said phenomenon;

detecting signals derived from said phenomenon during the course thereof;

repetitively convolving said signals with a transformation, establishing the temporal relation between initiation of said phenomenon and convolution of said signals so that the repetitive convolution produces an ordered set of first interferograms in which the sequence of the phenomenon and the convolution is temporally shifted in successive increments with respect to one another;

selecting from each interferogram of said set, a data moiety corresponding to a temporal resolution element occuring at a fixed position in time following said initiation during the course of said interferogram; and combining in a sequence according to the order of said set each of said data moieties so as to synthesize a second interferogram representing the convolution with said transformation of the signals from said phenomenon only at said fixed time position.

13. Method as defined in claim 12 including the step of inversely transforming said second interferogram so as to reconstitute date representing said signals occurring during said resolution elements at said fixed time positions.

* * * * *

UNITED STATES PATENT OFFICE
CERTIFICATE OF CORRECTION

PATENT NO. : 4,086,652
DATED     : April 25, 1978
INVENTOR(S) : Arlan Warren Mantz It is certified that error appears in the above-identified patent and that said Letters Patent are hereby corrected as shown below:

Claim 13, column 30, line 25, change "date" to --data--.

Signed and Sealed this

Twenty-ninth Day of August 1978

[SEAL]

Attest:

RUTH C. MASON
Attesting Officer

DONALD W. BANNER
Commissioner of Patents and Trademarks